（12） United States Patent
Ortner et al.

(10) Patent No.: US 9,157,869 B2
(45) Date of Patent: Oct. 13, 2015

(54) METHOD AND DEVICE FOR DETECTING CRACKS IN SEMICONDUCTOR SUBSTRATES

(75) Inventors: Andreas Ortner, Gau-Algesheim (DE);
Klaus Gerstner, Bischofsheim (DE);
Hilmar Von Campe, Bad Homburg (DE); Michael Stelzl, Mainz (DE)

(73) Assignee: SCHOTT AG, Mainz (DE)

( * ) Notice: Subject to any disclaimer, the term of this patent is extended or adjusted under 35 U.S.C. 154(b) by 434 days.

(21) Appl. No.: 13/504,289

(22) PCT Filed: Aug. 13, 2010

(86) PCT No.: PCT/EP2010/004980
§ 371 (c)(1),
(2), (4) Date: Jun. 18, 2012

(87) PCT Pub. No.: WO2011/050873
PCT Pub. Date: May 5, 2011

(65) Prior Publication Data
US 2012/0307236 A1    Dec. 6, 2012

(30) Foreign Application Priority Data
Oct. 26, 2009    (DE) .......................... 10 2009 050 711

(51) Int. Cl.
*G01N 21/00*    (2006.01)
*G01N 21/95*    (2006.01)

(52) U.S. Cl.
CPC .................................. *G01N 21/9505* (2013.01)

(58) Field of Classification Search
CPC ..................... G01N 21/896; G01N 2021/3568;
G01N 21/8806; G01N 2021/8809; G01N
2021/8841; G01N 21/9505
USPC ....................... 356/237.1–237.6, 239.3, 239.7
See application file for complete search history.

(56) References Cited

U.S. PATENT DOCUMENTS

| 5,355,213 | A  | * | 10/1994 | Dotan ......................... 356/239.7 |
| 5,781,230 | A  | * | 7/1998  | Nguyen et al. ................. 348/128 |
| 7,408,633 | B2 | * | 8/2008  | Nakajima et al. .......... 356/237.2 |
| 7,888,858 | B2 | * | 2/2011  | Cok et al. ....................... 313/503 |
| 8,055,058 | B2 | * | 11/2011 | Moon et al. ................... 382/145 |
| 8,077,305 | B2 | * | 12/2011 | Owen et al. ................ 356/237.1 |
| 2005/0231713 | A1 |   | 10/2005 | Owen et al. |

FOREIGN PATENT DOCUMENTS

| CN | 1536350 A | 10/2004 |
| CN | 1908638   | 2/2007  |
| DE | 146879    | 11/1903 |

(Continued)

OTHER PUBLICATIONS

Chinese Office Action dated Dec. 4, 2013 corresponding to Chinese App. No. 201080048527.1, 8 pp.

(Continued)

*Primary Examiner* — Michael A Lyons
*Assistant Examiner* — Shawn Decenzo
(74) *Attorney, Agent, or Firm* — Ohlandt, Greeley, Ruggiero & Perle, LLP

(57) ABSTRACT

A method and an apparatus for detecting cracks in semiconductor substrates, such as silicon wafers and solar cells, are provided. The method and apparatus are based on the detection of light deflected at a crack.

20 Claims, 9 Drawing Sheets

(56) References Cited

FOREIGN PATENT DOCUMENTS

| DE | 10316707 | 11/2004 |
| --- | --- | --- |
| JP | 8220008 | 8/1996 |
| KR | 10-2009-0107400 A | 10/2009 |
| TW | 200539489 A | 12/2005 |
| WO | 2008/112597 | 9/2008 |
| WO | 2009/125896 | 10/2009 |
| WO | 2009/125896 A1 | 10/2009 |

OTHER PUBLICATIONS

Fillard, J.P., "Laser Scanning Tomography: A Non-Destructive Test for Semiconductors", Journal de Physique, Sep. 1988, France, 8 pp.

Taijing, et al., "Observation of Microdefects and Microprecipitates in Si Crystals in IR Scattering Tomography", Journal of Crystal Growth 108 (1991) 482-490 pp, 9 pp.

Nango, et al., "Detection of Very Small Defects and Tiny Inclusions Just Under Mirror Polished Surfaces of Silicon Wafers by Inside Total Reflection", American Institute of Physics 1995, 2 pp.

Ogawa, et al., "Infrared Light Scattering Tomography With an Electical Streak Camera for Characterization of Semiconductor Crystals", American Institute of Physics 1986, 5 pp.

English Translation of German Office Action dated Sep. 30, 2013 corresponding to German Application No. 10 2009 050 711.6, 2 pp.

Office Action dated Sep. 28, 2012 corresponding to European Patent Application No. 2494339 with English translation.

Fillard, J. P., "Laser Scanning Tomography: A Non Destructive Qualification Test for Semiconductors;" Journal de Physique, Colloque C4, supplement au No. 9, Tome 49, Sep. 1988, 7 pp.

Taijing, L., et al., "Observation of microdefects and microprecepitates in Si Crystals by IR scattering tomography;" Journal of Crystal Growth, vol. 108, issue 3-4, Feb. 1, 1991, pp. 482-490.

Nango, N., et al., "Dectection of very small defects and tiny inclusions just under mirror polished surfaces of silicon wafers by inside total reflection;" J. Appl. Phys., vol. 78, No. 4, Aug. 1995, pp. 2982-2983.

Ogawa, T., et al., "Infrared light scattering tomography with an electrical streak camera for characterization of semiconductor crystals;" Rev. Sci. Instrum., vol. 57, No. 6, Jun. 1986, pp. 1135-1139.

International Search Report Dec. 15, 2010 corresponding to International Patent Application No. PCT/EP2010/004980.

English Translation of International Preliminary Report on Patentability corresponding to International Patent Application No. PCT/EP2010/004980.

Chinese Office Action dated Jul. 17, 2014 corresponding to Chinese Application No. 201080048527.1 with English translation, 18 pp.

Written Opinion of the International Searching Authority dated Dec. 15, 2010 for corresponding PCT/EP2010/004980, 6 pages.

Korean Office Action dated May 29, 2014 corresponding to Korean App. No. 20090107400, 12 pages.

* cited by examiner (a)    (b)

METHOD AND DEVICE FOR DETECTING CRACKS IN SEMICONDUCTOR SUBSTRATES

BACKGROUND

1. Field of the Invention

The invention generally relates to the detection of defects in semiconductor substrates. More particularly, the invention relates to the detection and localization of cracks in semiconductor substrates, such as in wafers.

2. Description of Related Art

For detecting cracks in semiconductor substrates, mechanical methods are known, in particular tactile and acoustic methods. For example, it is known from WO 2008/112597 A1 to compare the resonant frequencies of a silicon wafer with the resonant frequencies of a reference wafer. Deviations of the resonance frequencies are then considered to be indicative of cracks. A disadvantage herein is the mechanical stress that may possibly result in breaking, even of an intact wafer.

Moreover, optical methods are known. For example, the apparatus described in DE 01 46 879 A1 is based on a backlight arrangement. The wafer is irradiated with light at one side. On the opposite side a camera is arranged which detects the light passing through a crack. However, a requirement herein is that the crack extends through the wafer or is at least so deep that light can penetrate through the crack.

Other optical methods that use a similar arrangement are likewise based on a bright-field observation, wherein the wafer is irradiated with light at its rear face, which light, however, is transmitted through the wafer due to its wavelength for which the wafer is transparent. The wafer is then optically analyzed on the opposite side using a camera. At a crack, transmittance slightly varies so that the crack can be detected by the camera. Such an arrangement is known from JP 08220008 A. However, a drawback thereof is that the signal of transmittance variation is superimposed by a much stronger background signal in form of the light normally transmitted through the wafer. This makes detection difficult, especially for small cracks.

SUMMARY

An object of the invention, therefore, is to improve the detection of cracks in semiconductor substrates so as to avoid mechanical stress on the one hand, and a strong signal background on the other.

The method and apparatus of the invention are based on the detection of light deflected by a crack, or more generally, detection of electromagnetic radiation deflected by a crack.

Accordingly, the invention provides a method for detecting cracks in planar semiconductor substrates which have two opposite faces and a circumferential edge surface, wherein
  electromagnetic radiation, preferably infrared light, is directed into the edge surface of the semiconductor substrate, wherein
  the electromagnetic radiation, preferably the light, has a wavelength which is at least partially transmitted by the material of the semiconductor substrate, so that
  the electromagnetic radiation is directed from its point of incidence at the edge surface for at least half the distance to the opposite point of the edge surface by reflection at the faces, and wherein
  radiation is detected by means of an imaging optical detector which is sensitive to the introduced electromagnetic radiation, preferably the introduced light, which is scattered by a crack and exits from one of the faces at the crack site, and wherein an image of scattering intensity of at least a portion of the face that is viewed by the optical detector is generated from the signals captured by said optical detector.

Correspondingly, an apparatus for detecting cracks in planar semiconductor substrates having two opposite faces and a circumferential edge surface, which is adapted for performing the method described above comprises:
  means for supporting a semiconductor substrate; and a
  radiation source, preferably an infrared light source, which is arranged in relation to said means for supporting a semiconductor substrate in such a manner that electromagnetic radiation, preferably light, is directed into the edge surface of a supported semiconductor substrate, wherein the electromagnetic radiation, or the light, from the radiation source, or preferably the light source, has a wavelength which is at least partially transmitted by the material of the semiconductor substrate so that the radiation, or preferably the light, is directed from its point of incidence at the edge surface for at least half the distance to the opposite point of the edge surface by reflection at the faces; and
  an imaging optical detector sensitive to the introduced radiation, or preferably the introduced light, which is arranged in relation to the means for supporting a semiconductor substrate such that the optical detector detects radiation, or light, which is scattered at a crack and exits from one of the faces at the crack site of the semiconductor substrate; and
  a computing device adapted to generate an image of scattering intensity, or in case of a light source of scattering light intensity, of at least a portion of the face that is viewed by the optical detector, from the signals captured by the optical detector.

In contrast to prior art optical detectors, the semiconductor substrate, such as a semiconductor wafer, is not irradiated perpendicularly to the faces, rather the light is directed through the substrate along the faces. As long as the light is not scattered by a crack or another defect, total reflection occurs at the faces and the light is forwarded. Accordingly, only the defects substantially contribute to a signal detectable by the detector. In this way, a strong background is avoided during signal detection.

The choice of the light source depends inter alia on the semiconductor material of the substrate. Lasers are generally suitable due to their high light intensity and parallelism of the beam.

Semiconductors are typically transparent in the infrared range. This is also true for the technologically most relevant case of silicon substrates. Therefore, a preferred light source is an infrared laser which offers the additional advantage of a high light intensity. The laser, or the light therefrom, is directed onto the edge surface of the semiconductor substrate, after optionally having been formed previously, for example focused or collimated. Suitable infrared lasers, also for silicon substrates, are for example Nd:YAG lasers. In this case, the laser transitions at 1320 nm and 1444 nm can be used. However, laser diodes are especially preferred. They are much cheaper than Nd:YAG lasers, and moreover, laser diodes are available in the infrared range with wavelengths above the absorption edge of silicon.

Therefore, according to a refinement of the invention, the semiconductor substrate is irradiated using an infrared laser as the light source. In order to obtain full coverage of the semiconductor substrate notwithstanding the line-shaped irradiation thereof, the semiconductor substrate and the light source are moved relative to each other in a direction along the faces and transversely to the direction of incidence of the light, preferably by an advance means, during the illumination of the semiconductor substrate with the laser beam, such that the point of incidence of the light beam is moved along the edge of the semiconductor substrate, and the apparatus comprises computing means which are adapted to generate an image of that face of the semiconductor substrate which is viewed by the optical detector, from the detector signals recorded along the area of the semiconductor substrate irradiated by the laser beam during the advancement of the semiconductor substrate.

An imaging optical detector is generally understood as a detector which performs localized measurements in such a way that the measurement values can be combined to form an image of at least a portion of the surface. Thus, besides linear array cameras or area array cameras, scanners or optical detectors capturing the surface by scanning can be used, for example.

It is advantageous for the detection to be performed in localized manner, that is, not the total brightness of the light scattered out of one face of the semiconductor substrate is detected, but rather the light scattered out of a partial area. This makes sense because scattering may, to a limited extent, occur at non-defective points. The larger the captured area, the stronger gets the background signal. To perform a localized measurement, it is particularly preferred to detect the light scattered out of one face of the semiconductor substrate using an area array sensor or linear array sensor as an imaging sensor. So by means of the sensor a surface image of the local scattering light intensity can be determined, in which cracks exhibiting increased scattering then are clearly distinguished from its surroundings. More generally, a crack can therefore be determined from the image data obtained by the imaging optical detector through an evaluation of the local brightness distribution. One possible way, for example, is to analyze the images using an edge filter. Besides area array sensors or linear array sensors, sensors scanning the surface of the semiconductor substrate are suggested.

In a preferred embodiment, infrared light having a wavelength of at least 1.2 micrometers is directed from an appropriate light source onto the edge surface. That means, such light sources have wavelengths above the absorption edge of silicon which is at a wavelength of about 1.1 micrometers.

Again, a Nd:YAG laser is suitable which is set to a laser transition at a wavelength above the 1.2 micrometers mentioned above, or—more preferably—a laser diode.

Besides successive scanning of the semiconductor substrate using advance means and a localized light beam such as that particularly produced by an infrared laser, it is also possible, according to another embodiment of the invention, to irradiate a large portion of the semiconductor substrate or even the entire semiconductor substrate using a light beam widened along the edge surface. To this end, a radiation source, or preferably a light source, may be provided which generates a beam which illuminates at least one third of, preferably the entire width of the semiconductor substrate as measured along the direction perpendicular to the direction of incidence of the light. Detection of the scattering light may then be performed through line-wise scanning using the optical detector which is moved above the substrate during illumination. To achieve short measurement times, however, in a particularly preferred embodiment imaging of the surface of the semiconductor substrate is effected by an area array sensor as a component of the optical detector. Such a wide beam according to this embodiment of the invention may be provided, for example, by widening a laser beam in a direction parallel to the edge of the semiconductor substrate. Another possibility is to use an array of light emitting diodes. These may in particular be arranged in a line along the edge of the semiconductor substrate to so illuminate the edge surface.

Especially in case of local detection and/or local illumination of the substrate, it is furthermore preferred to provide an advance direction in which the semiconductor substrate is moved relative to the light source in a direction along the faces and transversely to the direction of incidence of the light, such that the point of incidence of the light beam is moved along the edge. In this way, the substrate moves past the detector, with constant illumination conditions, so that gradually the entire face of the substrate or at least the portion thereof which is relevant for further processing, is captured.

In particular, the light source may be fixedly arranged relative to the optical detector, with an advance means being provided for moving the semiconductor substrate relative to the arrangement of light source and optical detector, and the detector signals are recorded by a computing device. The successively acquired detector signals are then composed into a surface image. By means of the computing device the presence of a crack can then be detected from the local brightness distribution in the surface image.

Some semiconductor substrates are only partially transparent to suitable light. In order to have sufficient light intensity along the faces throughout the substrate to allow crack detection, a plurality of light beams may be used advantageously, which beams are introduced at different points of the edge.

In particular, it is suggested to introduce the light at opposite points of the edge. To this end, in a modification of the invention the radiation source, preferably light source, generates two opposing beams which traverse the substrate in opposite directions. This is useful even in case of a highly transparent substrate as a crack may act like a mirror. In this case, the light intensity will decrease rapidly behind the crack as viewed in the direction of irradiation, so that a possible further crack behind the first crack which acts as a mirror might not be detected any more. Yet another effect, also with transparent substrates, is that often strong scattering of the light occurs at its point of incidence at the substrate towards the detector. This may cause overdriving of the detector during scanning the peripheral region at the edge of the semiconductor substrate. If, however, different regions of the semiconductor substrate are irradiated by the opposed laser beams, the respective peripheral regions at the light exit points where overdriving does not occur may be captured by the optical detector. Then, a complete image of the surface may be produced from two partial images, wherein, when generating the partial images, the peripheral regions at the entry points of the laser beams are masked out. Accordingly, in one embodiment of the invention two opposite laser beams are directed through the semiconductor substrate, the scattered light of both laser beams is selectively captured using an imaging detector, and a partial image of the surface is produced from the respective selectively detected detector signals of the scattered light of each of the laser beams, and the partial images are composed into a complete image.

When looking to a polycrystalline semiconductor substrate such as a polycrystalline silicon wafer for solar cell production in a plan view, the individual crystallites and, correspondingly, the grain boundaries between the crystallites are clearly visible. Accordingly, a confusion of grain boundaries with cracks might be caused in front-light or back-light detection methods. In contrast thereto, it has surprisingly been found that with a polycrystalline semiconductor substrate even the grain boundaries virtually do not affect the measurement. Thus, confusion of a grain boundary with a crack is virtually impossible. Accordingly, in an advantageous embodiment of the invention, a polycrystalline semiconductor substrate is irradiated and checked for cracks.

Moreover, the method has been found particularly suitable for inspection of solar cells. It has been found that even contact fingers already applied do not interfere with the measurement. At the contact fingers additional scattering does not occur or at least not significantly, so that a confusion of a contact finger of the solar cell with a crack is avoided.

The invention distinguishes from known crack detection systems by a very high signal-to-noise ratio. This allows for a very quick inspection of semiconductor substrates such as, in particular, wafers and solar cells. It is perfectly possible to check substrates with an edge length of 156 millimeters within one second or less. Accordingly, in one embodiment of the invention, inspection is performed at an advance rate of at least 156 millimeters per second.

BRIEF DESCRIPTION OF THE DRAWINGS

The invention will now be explained in more detail with reference to the accompanying drawings, wherein the same reference numerals designate the same or similar elements.

In the drawings.

DETAILED DESCRIPTION

Figure 1:
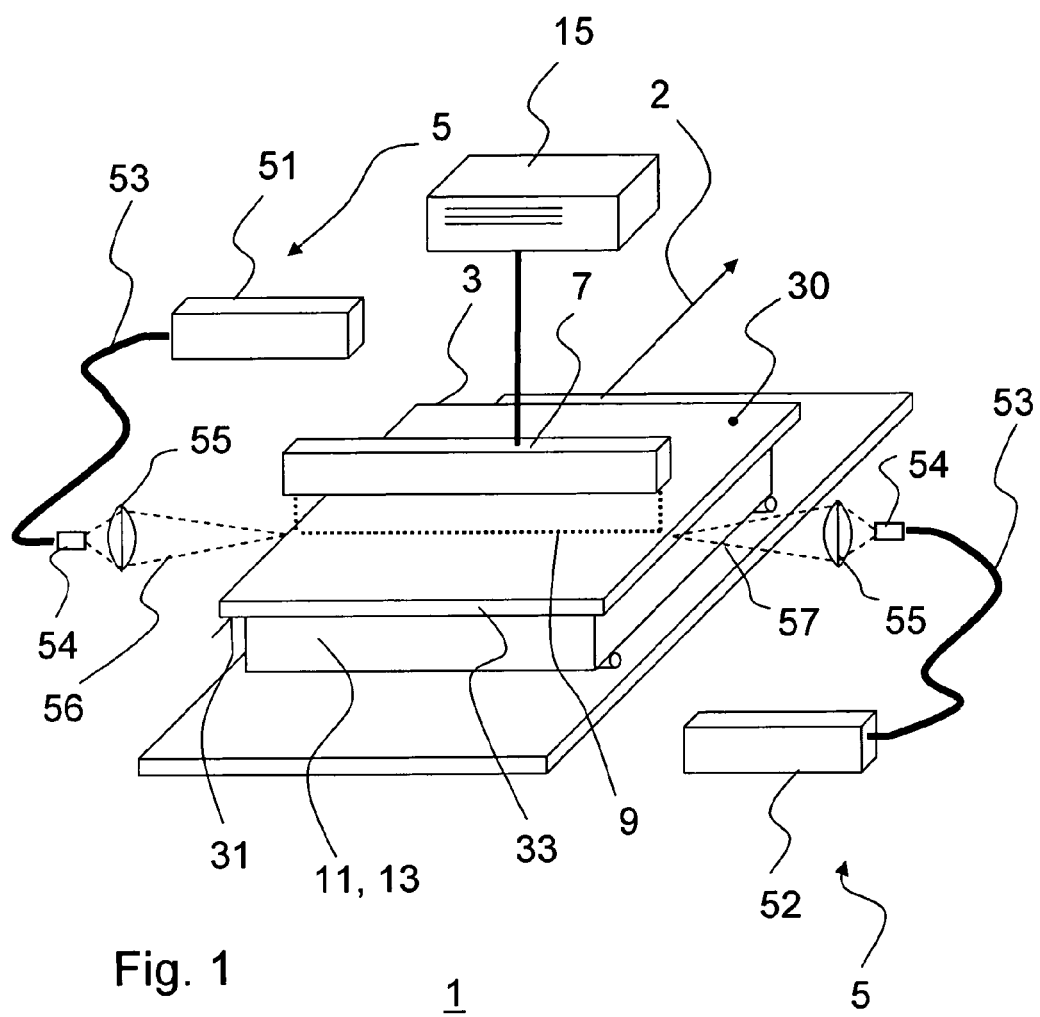
FIG. 1 schematically illustrates the configuration of an apparatus according to the invention.

FIG. 1 schematically shows the configuration of one exemplary embodiment of an apparatus 1 for detecting cracks in planar semiconductor substrates. A semiconductor substrate 3, for example a silicon wafer, is supported on suitable means 11. For this purpose, means 11 comprise a carriage on which semiconductor substrate 3 is placed. The carriage is movable along an advance direction 2 and so at the same time represents an advance means 13 by which the semiconductor substrate is moved through the apparatus.

Planar semiconductor substrate 3 has two opposing faces 30, 31 and a circumferential edge surface 33 with a height that corresponds to the thickness of semiconductor substrate 3.

Apparatus 1 comprises a light source for infrared light being designated by reference numeral 5 as a whole, which is arranged relative to means 11 or relative to a semiconductor substrate supported by means 11 such that the light therefrom is laterally introduced into edge surface 33. Semiconductor substrate 3 is at least partially transparent to the light from light source 5, so that the light is directed for at least half the way to the point of the edge opposite the incidence point, by total reflection at faces 30, 31 in a direction along these faces 30, 31.

In the example shown in FIG. 1, an infrared-sensitive linear array camera is provided as the optical detector 7, which captures a linear region 9 of face 30. Linear region 9 generally extends transversely, preferably but not necessarily perpendicular, to advance direction 2. With this arrangement, the linear array camera can detect light which is scattered by a crack and then exits from face 30 at the crack.

Instead of a linear array camera, an area array camera may be used, from which the respective area of the image field traversed by the laser beam is read-out.

Specifically, the light source here comprises two infrared lasers 51, 52. Suitable examples are Nd:YAG lasers which are set so that they emit at a wavelength of more than 1.2 micrometers. Especially, the laser transitions at wavelengths of 1320 and 1444 nanometers can be used. A power of about 10 milliwatts may already be sufficient to achieve appropriate irradiation of the semiconductor substrate. Without being limited to the exemplary embodiment illustrated in FIG. 1, one embodiment of the invention preferably provides an infrared laser with a radiation output of at least 5 milliwatts as part of the illumination source, for laterally irradiating a semiconductor wafer and to cause a sufficient light scattering signal at a crack. Preferably, however, laser diodes are used as a light source, since these are significantly cheaper than Nd:YAG lasers and available for the required range of wavelengths.

The displacement of semiconductor substrate 3 takes place along the surface of the substrate, so that in the course of advancement during the measurement laser beams 56, 57 always impinge at edge surface 33.

The linear array camera of optical detector 7 is connected to a computing device 15. Computing device 15 combines the detector signals successively obtained during advancement in form of image lines into a surface image.

To direct the light onto edge surface 33, optical fibers 53 with fiber outputs 54 are provided at infrared lasers 51, 52. In front of fiber outputs 54, beam-forming means 55 are arranged which focus and/or collimate beams 56, 57 onto opposite points of circumferential edge surface 33.

Figure 2:
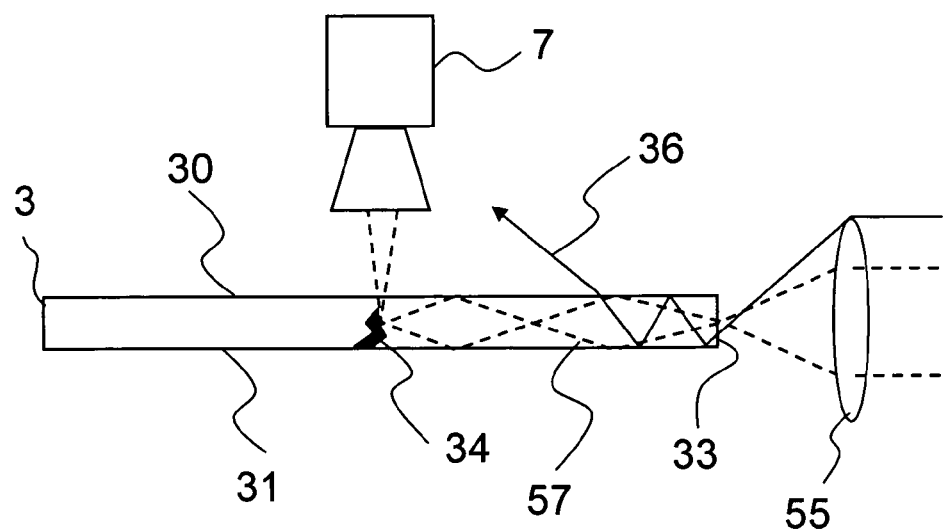
FIG. 2 shows the path of the rays in a semiconductor substrate having a crack.

FIG. 2 shows the path of rays in a semiconductor substrate 3 that has a crack 34. Laser beam 57 is directed into edge surface 33, as illustrated in FIG. 1. Within semiconductor substrate 3, laser beam 57 is directed by total reflection at faces 30, 31. Semiconductor substrate 3 has a crack 34. Crack 34 causes beam-deflecting effects such as scattering or reflection. So at crack 34 a portion of beam 57 is directed to the faces in such a large angle that the critical angle of total reflection is exceeded and the beam exits. The emerging light is then detected by optical detector 7 which views face 30. In the image of face 30, crack 34 appears as a brightly emerging structure.

Figure 3:
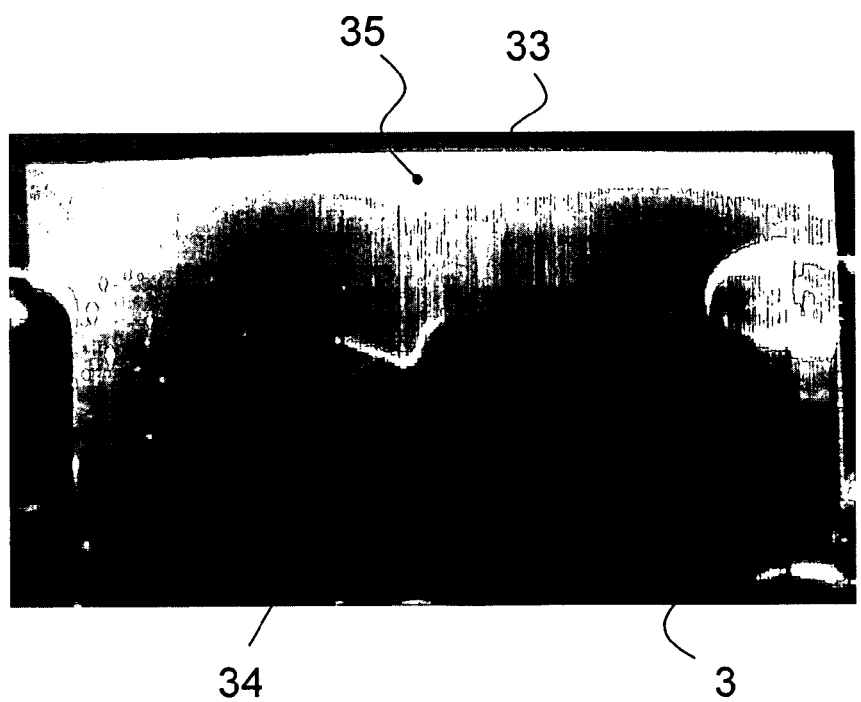
FIG. 3 shows an image of a wafer with a crack.

FIG. 3 shows an image of a solar cell wafer created by a combination of image lines. The image lines were successively captured during advancement using an infrared matrix camera. The array sensor of this camera is an InGaAs quantum detector. In this case, a line-shaped area of the sensor was selected for imaging the area irradiated by the laser beam. To increase the sensitivity of array sensors and hence the achievable scanning speed, averaging may be performed over several, e.g. three, adjacent image lines per image line of the surface image, which was done in the illustrated image.

In the image of FIG. 3, the laser beam was irradiated into the side of edge surface 33 shown at the top of the image.

As can be seen from FIG. 3, a crack 34 is easily detected with high contrast. Moreover, the contact fingers of the solar cell which are present on the surface of semiconductor substrate 3 do not interfere with the measurement.

However, in the vicinity of edge surface 33 to which the laser beam is directed, a bright region 35 can be seen in which overdriving of the sensor may occur. In this peripheral area cracks might not be recognized due to the overdrive. This overdrive in the peripheral region is mainly caused by rays which are directed into the semiconductor substrate at an angle greater than the angle for total reflection. Such a partial beam 36 which may exit after having been directed into semiconductor substrate 3, is depicted in FIG. 2.

Figure 4:
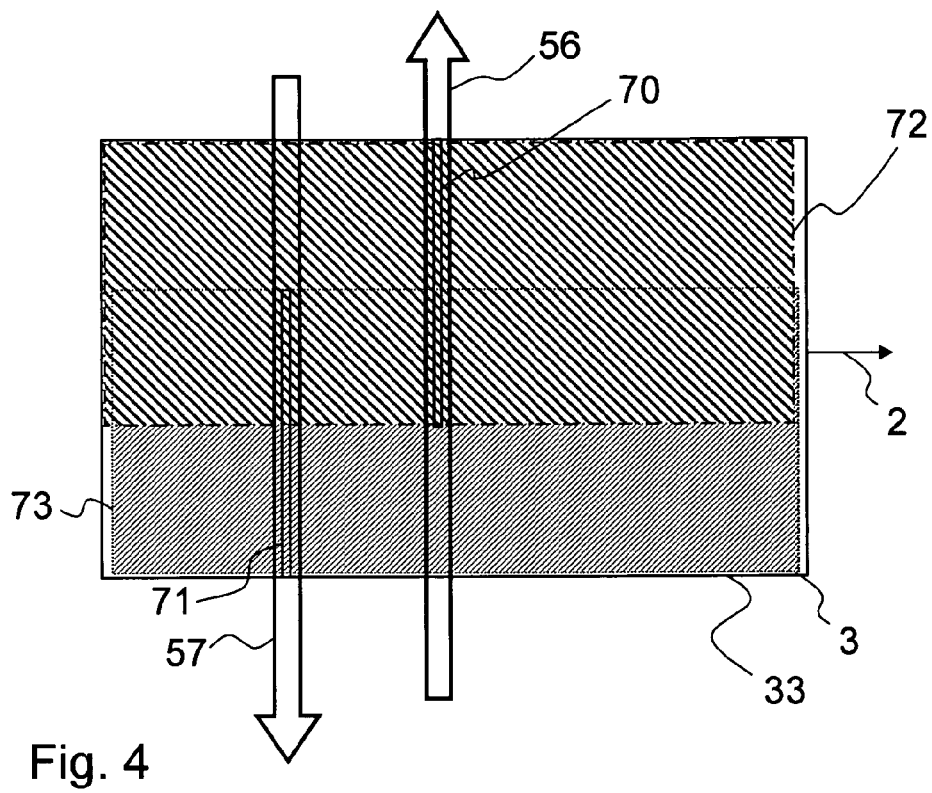
FIG. 4 illustrates, in a plan view of a semiconductor substrate, an arrangement for crack detection.

In principle, this effect can be addressed by appropriate collimation and/or focusing. Another alternative or additional possibility in an arrangement such as shown in FIG. 1 with two opposing laser beams is illustrated in the arrangement of FIG. 4. The measuring principle of the arrangement illustrated in FIG. 4 is based on directing two opposing laser beams through the substrate, selectively detecting the scattering light of the two laser beams with an imaging detector, and generating a respective partial image of the surface from the selectively captured detector signals of each of the laser beams, and combining the partial images into a complete image.

Without being limited to the embodiment shown in FIG. 4, for producing the partial images it is preferred here to direct the two laser beams 56, 57 through the semiconductor substrate 3 well in opposite directions, but offset to each other in the advance direction.

Preferably, an area array sensor is used to produce the scattering light image. It is also possible to provide a line scan camera for each of the portions irradiated by laser beams 56, 57. In case of an area array sensor, two line-shaped areas 70, 71 onto which the regions of semiconductor substrate 3 illuminated by laser beams 56, 57 are imaged are read out from the sensor. For example, two or more adjacent image lines may be read out as areas 70, 71. Furthermore, to improve the signal-to-noise ratio averaging may be performed between 2 adjacent pixels along the advancement direction across the plurality of image lines.

As can be seen from FIG. 4, the image lines are not assessed over the entire length of the irradiated regions. Rather, for both beams 56, 57 the periphery of the semiconductor substrate where the respective beam enters is omitted.

On the other hand, the excessively irradiated or overdriven region at the edge of the semiconductor substrate may also be assessed. If there are cracks in this region these may cause shadowing effects that are visible in the image as a bright-dark edge.

During the advancement of the semiconductor substrate the two line-shaped areas 70, 71 are then cyclically or successively read out. The read-out line-shaped areas 70, 71, or the signals therefrom, may then be composed into two partial images 72, 73, with partial image 72 composed from read-out line-shaped areas 70, and partial image 73 from read-out line-shaped areas 71. The two partial images 70, 71 may then be combined into an overall image of the scattering light distribution. The two partial images 72, 73 may overlap, as shown in the example of FIG. 4. This may be favorable in order to facilitate the combination of partial images 72, 73 or to avoid artifacts at an interface of the partial images.

Figure 5:
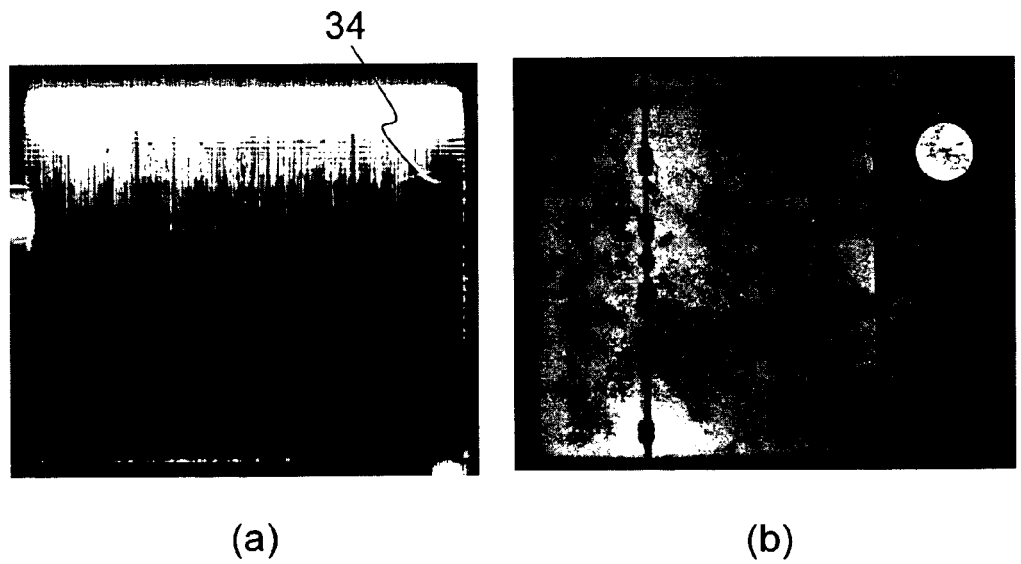
FIG. 5 shows a comparison of an imaged surface of a solar cell and an electroluminescence image.

Another widely used test method applied for solar cells is a photographical image of electroluminescence. In this case the solar cell is operated inversely, like a light emitting diode, and the emitted electroluminescence light is captured. FIG. 5 shows a comparison of the results of this procedure and of crack detection according to the invention. The left image designated (a) is an image of a solar cell having a crack 34. The image designated (b) on the right hand side is an electroluminescence image of the solar cell. It is noticeable that the crack can barely be seen in the electroluminescence image. A circular area of the image where the crack runs has been highlighted in terms of contrast. Even with the enhanced contrast the crack is barely visible. Moreover, variations in brightness are caused by the polycrystalline structure.

In the electroluminescence procedure, brightness contrasts of adjacent areas are produced with alternating radiative and non-radiative recombinations.

Besides radiative recombination of electron-hole pairs (luminescence), non-radiative recombination occurs at crystal defects such as recombination-active grain boundaries or offsets. Also, cracks may become visible due to non-radiative recombination in the vicinity of the crack.

Other bright/dark contrasts result from interrupted current paths such as broken conductors, e.g. the individual fingers of the front grid. Also, disorders of the surface are reflected in the electroluminescence image as a dark contrast.

To distinguish between these various causes of contrasts, attempts are made to differentiate between cracks and the other structures by image analyzing algorithms. However, these can only be performed based on an examination of shapes or contrasts, so that the method is currently not effective and leads to substantial misidentifications.

Own investigations which were very time-consuming and combined electroluminescence images with microscopy and electron microscopy have shown that in case of very narrow cracks unambiguous identification was not possible in all cases, that means, not all macroscopic cracks assumed from the electroluminescence image were identified using the above methods.

In contrast, when using the present invention unambiguous identification of exactly these cracks was possible in a simple and rapid manner.

Therefore, a great advantage of a combination of electroluminescence imaging and the crack detection method according to the invention is that in only one detection operation and with one experimental arrangement
1. all relevant disorders of the solar cell can be detected;
2. cracks among them can easily be detected; and
3. defective solar cells can be discarded according to clear criteria.

An unsafe mathematical formalism can be replaced by the unambiguous identification method, resulting in a significant increase in yield of good cells in a production process.

For crack detection in solar wafers, an analog way for unambiguous identification and discarding results from the possibility of combining photoluminescence images, and/or infrared backlight images with illumination of the rear face in a bright-field and/or dark-field arrangement, and/or microwave lifetime mappings, and the invention.

Figure 6A:
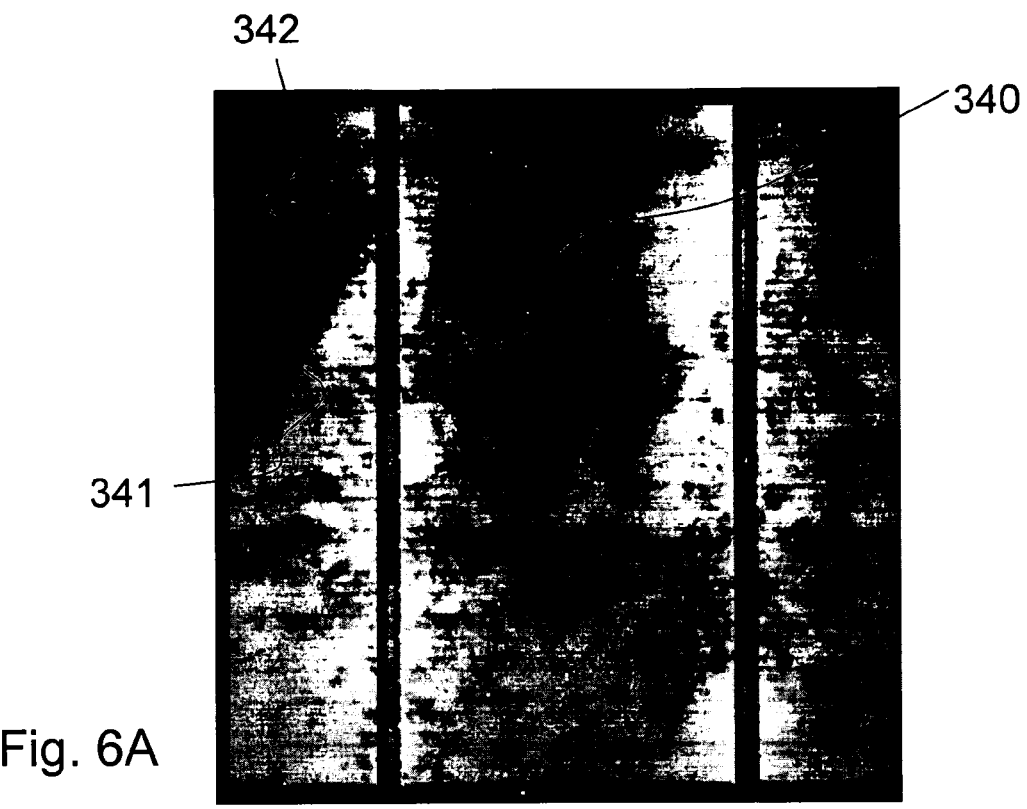
FIG. 6A is an electroluminescence image of a solar cell.
Figure 6B:
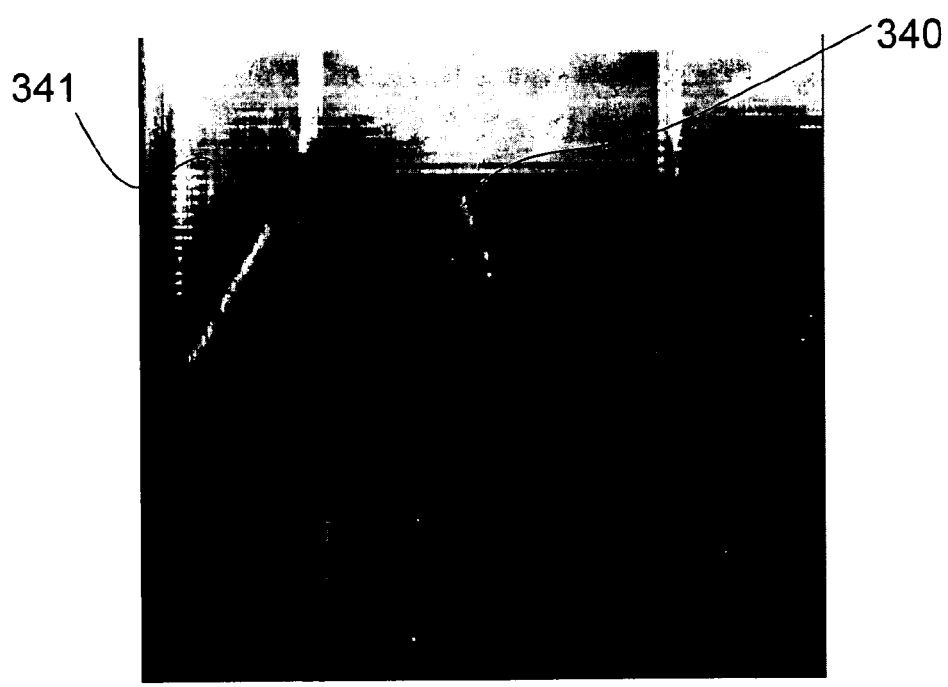
FIG. 6B is a superposition of the image shown in FIG. 6A and a scattering light image.

For illustration purposes, FIG. 6A shows another electroluminescence image of a solar cell with cracks. The solar cell has two cracks 340, 341. 6B shows an image montage of an electroluminescence image with a scattering light image according to the crack detection of the invention with lateral irradiation. In FIG. 6B, the structures of the electroluminescence image appear as dark contrasts, the cracks appear as bright lines.

Therefore, a refinement of the invention proposes combining the inventive irradiation method with an electroluminescence image and/or the other methods of infrared irradiation mentioned above. So according to this embodiment of the invention, in addition to scattering light imaging, at least one of electroluminescence imaging, photoluminescence imaging, bright- or dark-field imaging, in particular with back-light or front-light, is performed. Here, back-light illumination with infrared light means illumination of the face of the semiconductor substrate opposite the face viewed by the optical detector. In this way, a bright-field image is produced.

In this manner, other defects besides cracks, such as especially delamination of contacts can be recognized immediately. If electrical connection of the connecting structures, typically contact strips and contact fingers, is defective or interrupted, this can be detected quickly and reliably from an electroluminescence image, from a local or global darkening in the electroluminescence image. In the image shown in FIG. 6A, for example, crack 341 also interrupts the contact connection of the solar cell in the area 342 to the left of the crack. This non-contacted area 342 therefore appears dark in the electroluminescence image.

Figure 7:
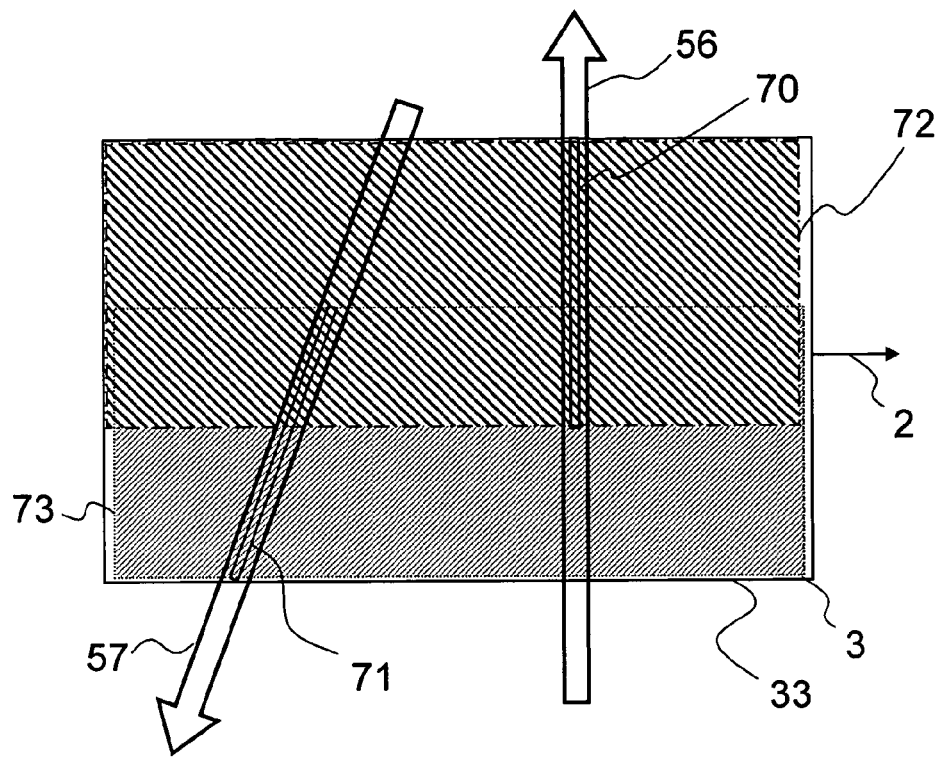
FIG. 7 illustrates an arrangement with a laser beam irradiating the semiconductor substrate obliquely to the advance direction.

If a crack runs in parallel to the irradiation direction of the beam, scattering efficiency might be very low, so that such an effect might not be reliably detectable in spite of the contrast achievable by the measurement method according to the invention. To prevent this, it may be useful to illuminate the semiconductor substrate with a laser beam transversely to the advance direction. FIG. 7 similar to FIG. 4 shows such a configuration in a plan view; the semiconductor substrate 3 in this example is again irradiated by two laser beams 56, 57, and at least one of laser beams, laser beam 57 in this case, illuminates semiconductor substrate 3 obliquely to the advance direction.

Figure 8:
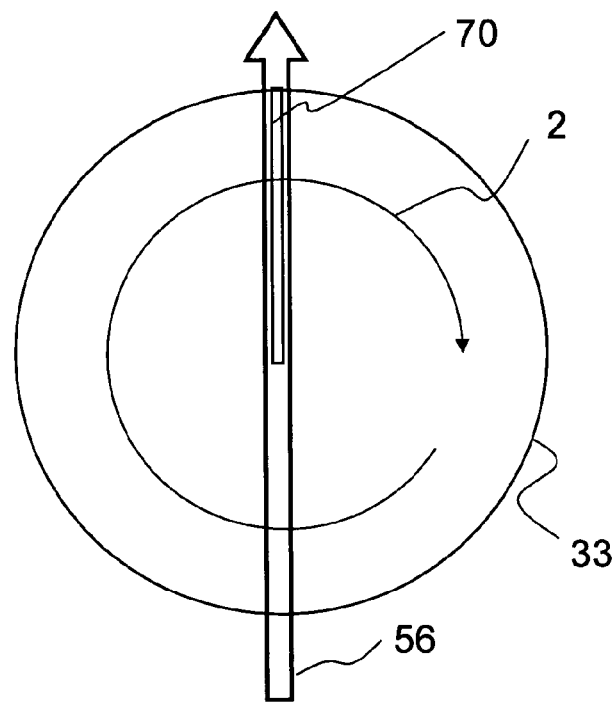
FIG. 8 illustrates an arrangement with a rotating semiconductor substrate.

In the previous examples, semiconductor substrate 3 and the laser beams were guided relative to each other in translation past one another. However, the advance direction may also be a rotation. Such movement is particularly useful in case of round wafers such as often used for manufacturing electronic components and integrated circuits. FIG. 8 shows a plan view of such an arrangement. Here, the edge surface 33 of round semiconductor substrate 3 is moved past laser beam 56 by rotation along circular advance direction 2. This offers the advantage that the distance between edge surface 33 and the laser can be kept constant, as in case of a rectilinear edge surface and translational advancement. To obtain an overall image of the semiconductor substrate, for example a line-shaped area may be selected in the sensor, which extends from the light exit point at edge surface 33 to the center of rotation or beyond.

Figure 9:
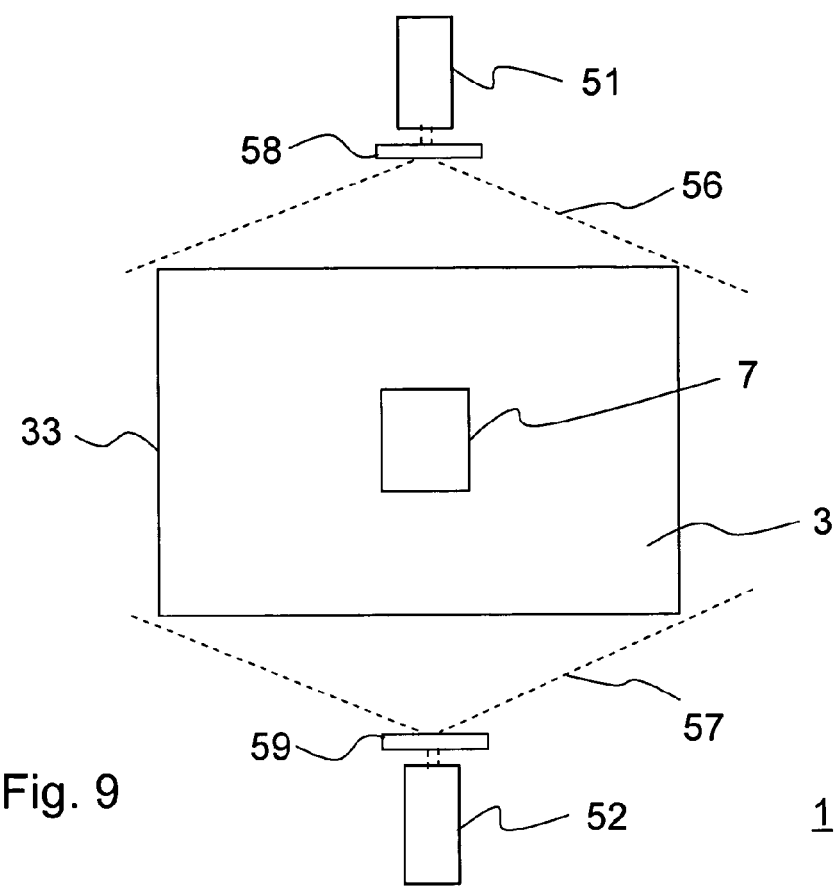
FIGS. 9 and 10 show two variations of the apparatus shown in FIG. 1.
Figure 10:
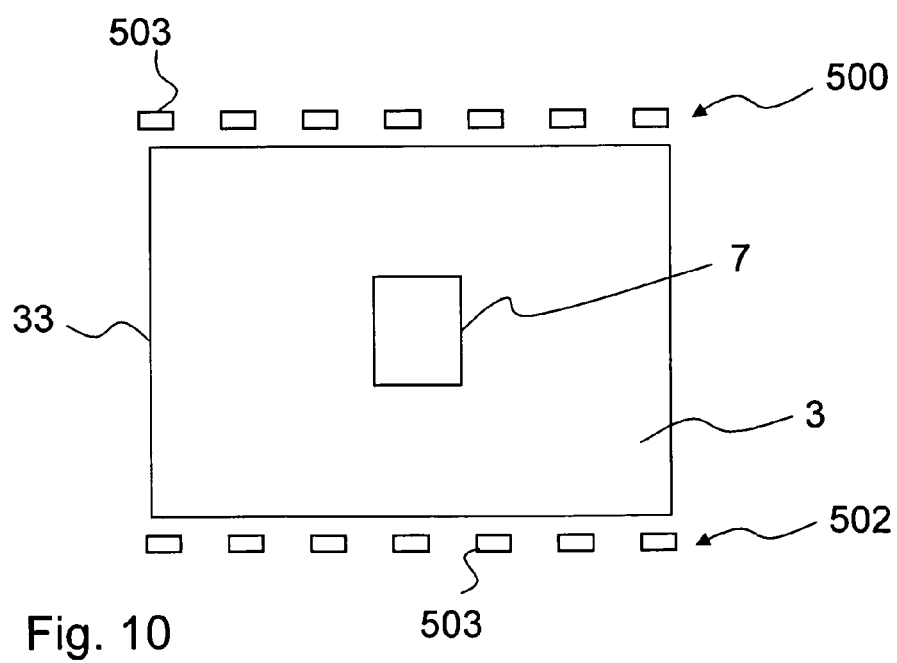

FIGS. 9 and 10 show, in a plan view, two variations of apparatus 1 illustrated in FIG. 1. Both variations are based on a light source which produces two beams, each of which illuminates the entire width of the semiconductor substrate as measured along the direction perpendicular to the direction of incidence of the light.

The variation of apparatus 1 shown in FIG. 9 uses two infrared laser 51, 52 similar to the embodiment shown in FIG. 1 which illuminate the edge surface 33 of semiconductor substrate 3 from opposite sides. Additionally, beam widening means 58, 59 are provided for widening laser beams 56, 57 in a direction along the edge. Beams 56, 57 are widened so much that each of the beams directed into semiconductor substrate 3 completely irradiates the semiconductor substrate. So optical detector 7 can obtain a complete image of the scattering light distribution with a single shot. To avoid the effect of excessive irradiation as seen in FIG. 3, two images may be taken for which lasers 56, 57 are turned off alternately, so that for each image the semiconductor substrate is illuminated by a different laser.

For widening the beam, appropriate diffractive optical elements or cylindrical lenses may be used, for example, as beam widening means 58, 59. Another possibility is to use an optical fiber array.

In the variation of FIG. 10, two lines 500, 502 of light emitting diodes 503 are used instead of the lasers. In the illustrated embodiment, the light emitting diodes are arranged in lines that extend along the edges surface 33. Generation of an overall image of scattering light distribution may be performed similarly to the example shown in the FIG. 9 by alternately operating lines 500, 502, to avoid any effect of excessive irradiation. Light emitting diodes that can be used for this embodiment are available with wavelengths of 1200 nanometers and more, as well as laser diodes.

In the exemplary embodiment shown in FIG. 4, the two laser beams 56, 57 were directed through semiconductor substrate 3 in opposite directions, but offset along the advance direction.

Figure 11:
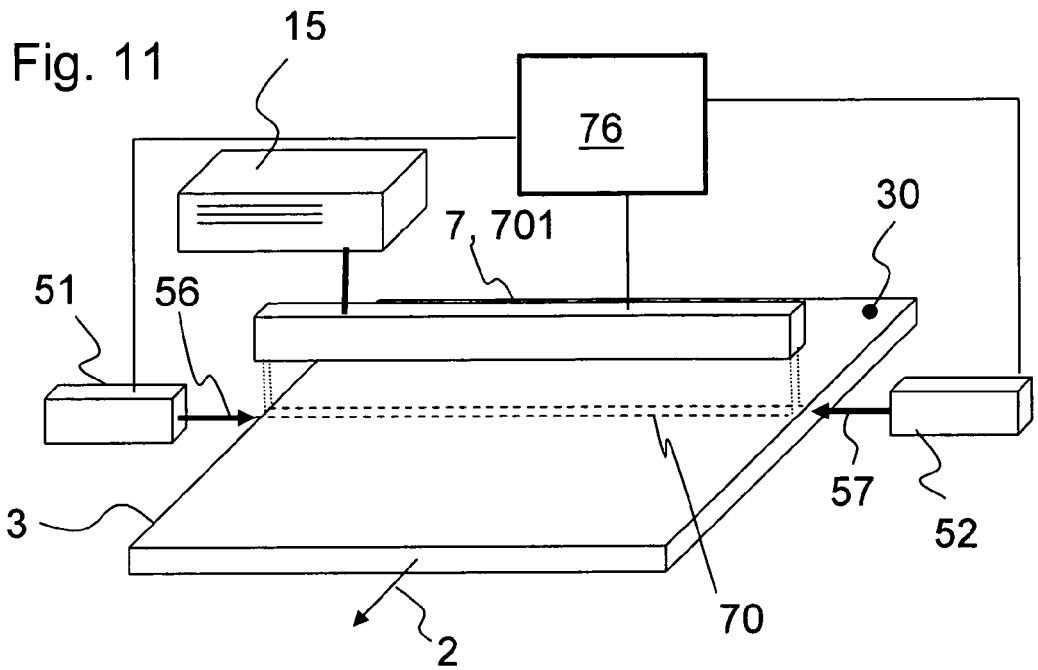
FIG. 11 illustrates a variation of the embodiment shown in FIG. 4, with intermittently clocked, opposing, coaxial light beams.

FIG. 11 shows another embodiment which is based on intermittent illumination, again using two opposing light beams 56, 57. For this purpose, a trigger means 76 is provided and adapted for intermittently synchronizing the two beams. The two radiation sources, preferably light sources, more preferably lasers, illuminate the measuring object from opposite sides in co-linear or coaxial direction, however not simultaneously, but alternately. To obtain high measurement frequencies, laser sources are preferred that can be modulated.

Figure 12:
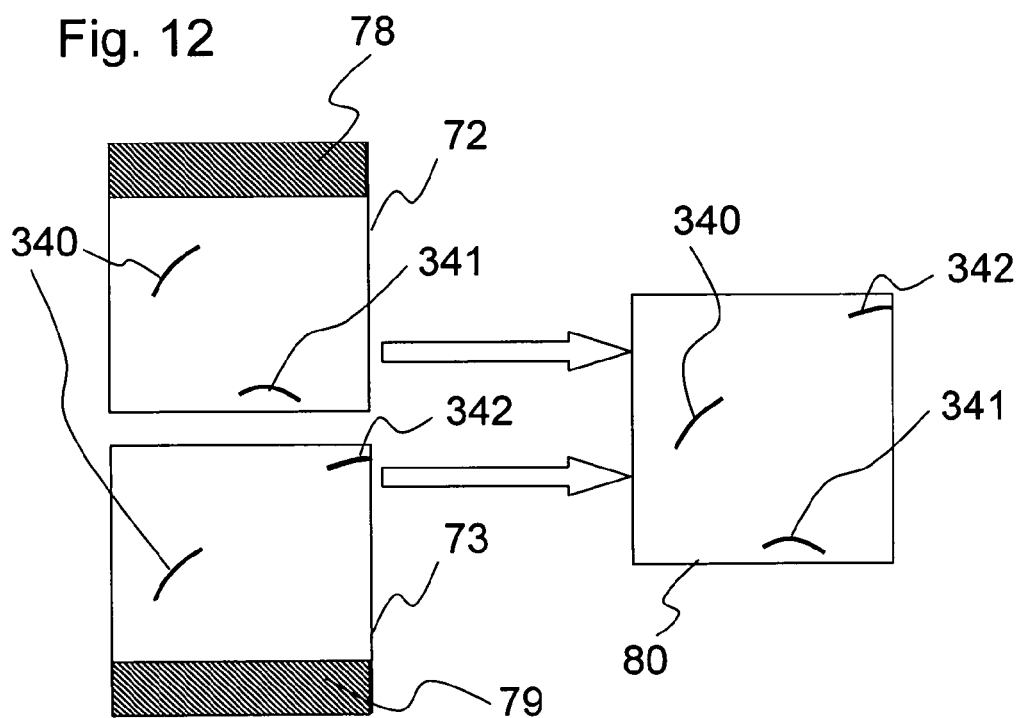
FIG. 12 illustrates combination of partial images as obtained with the arrangement shown in FIG. 11 into a complete image.

Trigger means 76 operates optical detector 7 in synchronism with the clocking of the two beams, so that the detector intermittently generates detector signals of the scattering light from the first light beam 56 and the second light beam 57, respectively. A suitable detector for this purpose is a line scan camera 701. Light beams 56, 57 here not only extend in opposite directions, but also coaxially. As in the previous examples, a computing device 15 is provided which combines the detector signals successively obtained in form of image lines during the advancement into a surface image. Here the peripheral regions of semiconductor substrate 3 in which overdriving occurs upon light input, may be replaced by image data which are obtained by the light beam introduced at the opposite side and emerging at the respective peripheral region. The image lines captured for each of the light pulses of the two light beams 56, 57 may be directly assembled into the overall image line by line, or two partial images may be produced from multiple image lines, which are then joined together. FIG. 12 illustrates joining of the two partial images 72, 73 each of which represents the scattering light intensity of one of the two light beams 56, 57, into a total image 80. For assembling a complete image, only a portion of the detector signals of each of partial images 72, 73 is taken into account, so that strips 78, 79 are omitted in which overdrive occurs at the light input region of semiconductor substrate 3. However, as mentioned before, the overdriven areas may additionally be assessed for the presence of cracks, by checking for shadowed areas caused by cracks.

An advantage of this two-channel, clocked measuring apparatus with opposed measurement beams is that the detector signals alternately obtained for the two light beams 56, 57 belong to the same line-shaped area 70. Shifting of the partial images prior to their assembly so that they fit together can therefore be dispensed with when composing the complete image.

The use of an infrared area array detector, besides its high cost compared with a line scan camera has the other disadvantages of a reduced spatial resolution and lower measuring frequency (image capturing rate), i.e. at least partial images or the complete image have to be read and evaluated. Modern infrared line scan cameras offer the advantages of high image resolution (high pixel count per unit length) and typically of significantly higher line frequencies at lower cost, when compared to area array detectors.

Control of the light sources, preferably infrared lasers 51, 52, in particular in terms of modulation, exposure time, laser power, and of line scan camera 701 may be effected by means of suitable trigger signals such as TTL signals. According to one exemplary embodiment, image acquisition by line scan camera 701 during each individual illumination cycle may be performed by a CameraLink (CL) frame grabber which, by means of suitable software or in form of a programmed FPGA, assembles the read-in line data of the camera into two images of the measurement object under the different illumination conditions.

Each of the two images is evaluated for defects in the measurement object, such as cracks 340, 341 shown in FIG. 12, and allows for detection of defects, also in the peripheral region of the respective non-illuminated edge of the measuring object, i.e. semiconductor substrate 3, so that in total all edges of semiconductor substrate 3 are inspected. If evaluation is performed separately in the two partial images 72 and 73, assembly into a total image, such as shown in FIG. 12, is not absolutely necessary.

As mentioned above, the invention may be combined with other measurement methods, such as capturing electroluminescence images, infrared back-light images with illumination of the rear face, microwave lifetime mapping, as well as front-light images. This is in particular possible when extending the apparatus described above in terms of pulsed, intermittent signal recording. This modification of the invention will be explained in more detail below. The modification of the invention is based on alternately recording light signals of the one, or as in the embodiment of FIG. 11 two, pulsed laterally irradiating infrared light sources and of at least one further light signal of another light source. From the intermittently obtained signals of the light sources, respective images of the measurement object, in this case of the semiconductor substrate, can then be produced which correspond to the different light sources. In case of electroluminescence and microwave-excited lifetime mapping, the semiconductor substrate itself is the source of light.

For detecting other light signals, besides the detection of scattering light under lateral irradiation according to the invention, further trigger signals are provided. Accordingly, in one embodiment of the invention a trigger means 76 is provided which outputs trigger signals clocking detector 7 in synchronism with infrared light source 5, the trigger means 76 additionally outputting other trigger pulses to detector 7 in the intervals between those trigger pulses which clock the detector synchronously with the infrared light source, so that detector 7 detects light of the other light source during each of the periods in which infrared light source 5 is off. The other light source can be another laser beam directed into the opposite edge in opposite direction, as explained in the example of FIG. 11. In addition, other light sources may be employed which are operated in a triggered or optionally non-triggered mode. If a non-triggered light source is used which therefore also provides light signals while the scattering light from the triggered, laterally irradiating infrared light source is recorded, the respective signals of the light sources may then be extracted by simple subtraction of the detector signals.

Figure 13:
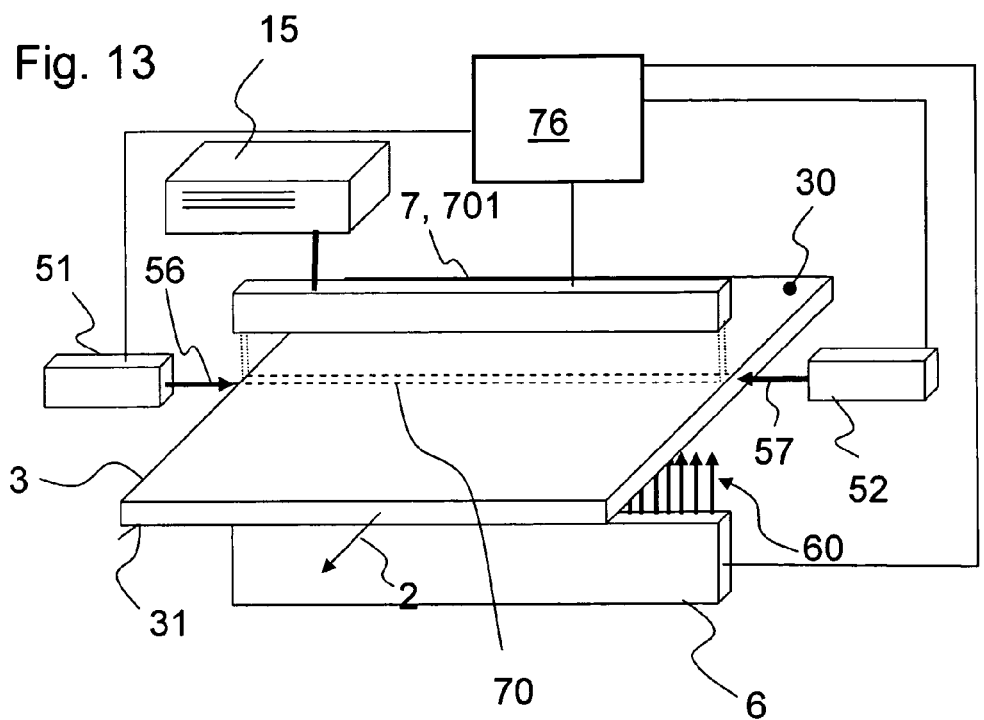
FIG. 13 illustrates a modification of the embodiment shown in FIG. 11.

An exemplary arrangement will be explained with reference to FIGS. 13 and 14. The arrangement of the apparatus of FIG. 13 corresponds to that of the embodiment of FIG. 11. In addition to the two lasers 51, 52 coupled into opposite edge surfaces of semiconductor substrate 3, another light source is provided in form of a bright-field infrared light source 6. This bright-field infrared light source 6 illuminates face 31 opposite face 30 that is viewed by optical detector 7, or in this case line scan camera 701, with a light beam 60. Suitably, light beam 60 is widened into a fan-shape, so that the line-shaped area captured by line scan camera 7 is entirely illuminated by light beam 60 from the rear face.

For this purpose, for example, the light from an IR light source, optionally guided by an optical fiber, may be directed onto the rear face 31 of semiconductor substrate 3 as seen from the camera using a rod lens, so that line scan camera 701 captures a back-light image of the wafer. Besides the exemplary arrangement shown in FIG. 13 for additionally taking back-light bright-field images, combinations with other measurement methods such as back-light dark-field images, photoluminescence, and electroluminescence are possible. For a back-light dark-field image, the light beam from light source 6 is directed to rear face 31 as seen from optical detector 7 in such a manner that in case of an undisturbed passage the light is directed past optical detector 7.

Control of all light sources and of image acquisition by the infrared sensor may again be effected using a CL frame grabber and appropriate software. Advantages of a combination of the irradiation of the edge surfaces according to the invention with other IR back-light images are the enhanced detection capabilities in terms of defects such as scratches, holes, inclusions, etc.

For controlling bright-field infrared light source 6, the latter is connected to trigger means 76, like the two infrared laser 51, 52.

Figure 14:
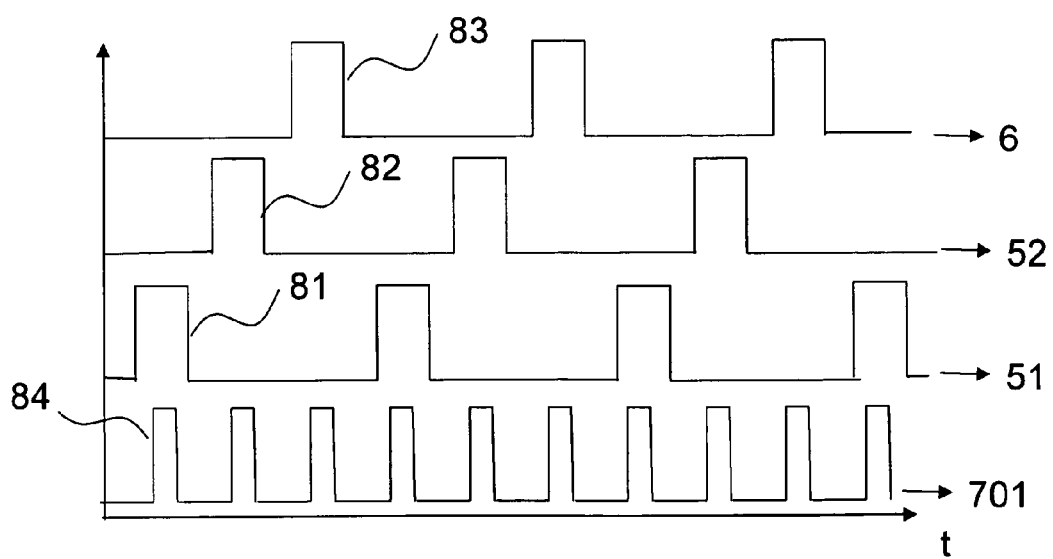
FIG. 14 shows a time sequence of trigger signals.

An exemplary time sequence of the trigger or clock signals outputted by trigger means 76 is shown in FIG. 14. Next to the four illustrated trigger pulse series, the reference numerals of those components are given to which the trigger pulses are sent. Accordingly, the uppermost pulse sequence illustrated in the diagram is transmitted by trigger means to bright-field light source 6, the sequence illustrated directly below is transmitted to second infrared laser 52, the sequence in turn illustrated below the latter is transmitted to first infrared laser 51, and the lowermost sequence to the optical detector 7, or specifically, line scan camera 701. As can be seen, trigger pulses 81, 82, 83 of the pulse sequences which are transmitted to light sources 6, 51, 52 and cause the respective light source to be switched on for the duration of the pulses, are offset in time relative to each other, so that the light sources are operated intermittently. Trigger pulses 84 which are transmitted to line scan camera 710 are time-synchronized to trigger pulses 81, 82, 83, respectively, so that each time one of light sources 6, 51, 52 is switched on, an image line is recorded by line scan camera 701.

Accordingly, in the time intervals between the trigger pulses that drive detector 7, or in the present case in particular line scan camera 701, in synchronism with infrared light source 5, or in the present case infrared laser 51 or infrared laser 52, further clock pulses are outputted by trigger means

76 to detector 7, so that detector 7 detects the light from another light source (in the example of FIG. 13 corresponding to bright-field light source 6) during each period in which the infrared light source 5 (i.e. infrared lasers 51, 52 in the example of FIG. 13) is switched off. Of course, in the example shown in FIG. 13, bright-field light source 6 may be replaced by or supplemented with other light sources. If additional light sources are used, the timing of the trigger pulses such as exemplified in FIG. 14 may be adjusted accordingly, so that image lines are successively recorded under illumination of the sequentially enabled light sources.

Figure 15:
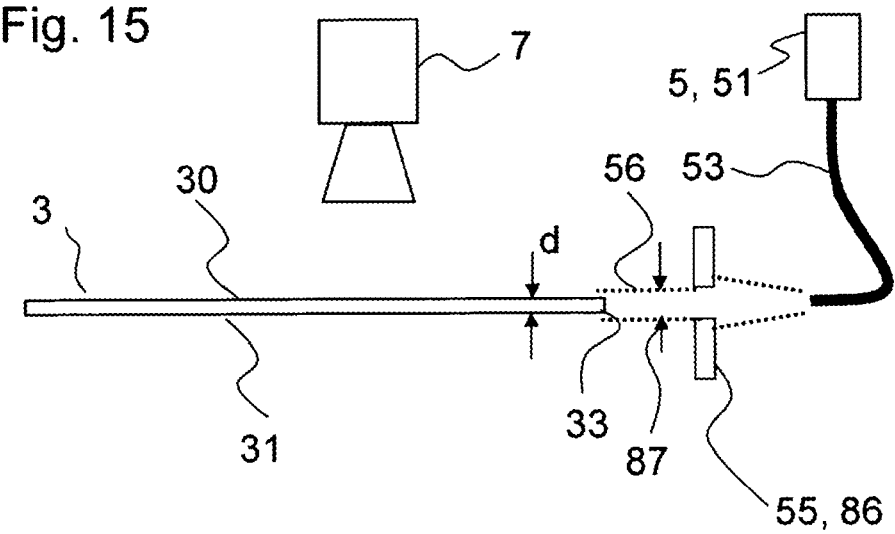
FIG. 15 illustrates one exemplary embodiment for introducing light into the edge face of the semiconductor substrate.

In the exemplary embodiments shown in FIGS. 1 and 2, focusing means were used as beam-forming means 55 which focus beams 56, 57 from light source 5 onto opposite points of the circumferential edge surface 33. FIG. 15 illustrates an alternative for directing the light into edge surface 33. The parallel light beam 56 from light source 5 is not focused onto edge surface 33 in a manner that the diameter of the beam spot on edge surface 33 would be smaller than the thickness of semiconductor substrate 3. Rather, by means of a suitably designed light source 5 a light beam 56 is directed onto edge surface 33 whose extent on edge surface 33 in the direction perpendicular to the faces is generally greater than the thickness d of semiconductor substrate 3.

In the example shown in FIG. 15, a collimator 86 is provided as beam-forming means 55 and is arranged in front of the output end of optical fiber 53. The collimator produces a parallel or at least approximately parallel light beam 56. The beam diameter 87 thereof, despite collimation, is greater than the thickness d of semiconductor substrate 3, i.e. the spacing between faces 30, 31. The use of a light beam 56 with such a great extension for inspecting semiconductor substrates ensures introduction of light into semiconductor substrate 3 even in case of an alteration of the position of semiconductor substrate 3 in a direction perpendicular to the faces.

A parallel beam as produced by the collimator in the example shown in FIG. 15 is moreover favorable to make the introduction of light less sensitive to positional alterations in a direction along the incidence of the light, since the parallelized beam has the lowest possible divergence. These measures, i.e., generally, introducing a parallel light beam having a beam dimension which in the direction perpendicular to the faces is greater than the thickness of the semiconductor substrate, maximize the depth of the measuring field and make the arrangement relatively insensitive in terms of orientation of the semiconductor substrate.

Preferably, the dimension of the light beam perpendicular to the faces (i.e. the beam diameter, in case of a circular light beam) is larger than the thickness of semiconductor substrate 3 by at least 1.5 times, more preferably by at least 3 times. For example, in case the semiconductor substrate 3 has a thickness of 200 micrometers, a beam with a beam diameter of 800 micrometers may be used.

Figure 16:
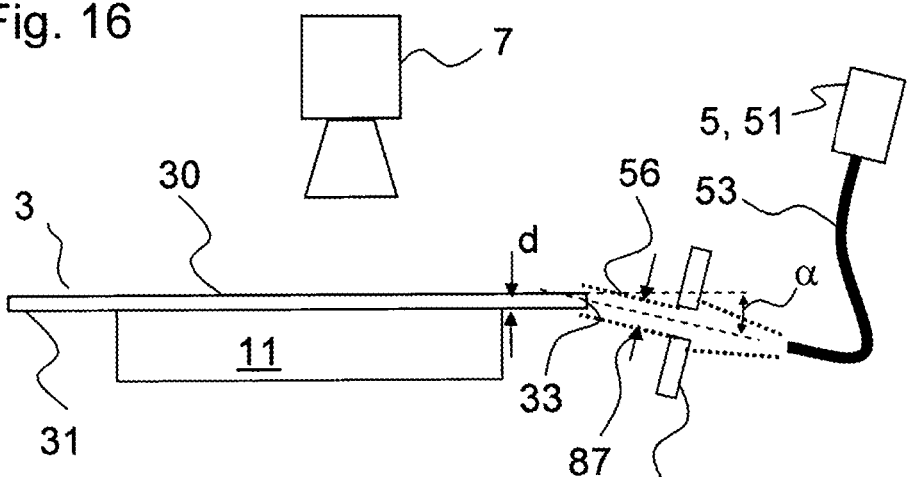
FIG. 16 illustrates another exemplary embodiment of introducing the light.

FIG. 16 shows another variation of light input which may similarly be applied to the focusing of the light beam onto the edge surface as shown in FIGS. 1 and 2. As can be seen from FIG. 16, the light source is arranged such that light beam 56 obliquely impinges at edge 33 of semiconductor substrate 3, or at an angle to the planes of faces 30, 31. Such oblique illumination of semiconductor substrate 3 has proved to be advantageous to minimize disturbing illumination effects, such as reflections of stray light by the surface of semiconductor substrate 3 or at means 11 for supporting the semiconductor substrate 3. This oblique illumination is particularly advantageous if, as in the example of FIG. 15, a light beam is used, whose dimension at edge surface 33 in the direction perpendicular to faces 30, 31 is greater than the thickness d of the semiconductor substrate 3. Illumination in parallel to faces 30, 31, as shown in FIG. 15, may cause light scattering of portions of the light beam 56 that are directed past semiconductor substrate 3 above and below the latter, at any structures on faces 30, 31. Examples of such structures are overall roughness as well as contacts and busbars such as those often present on solar cells. These scattered light components may also be detected by optical detector 7 which could possibly lead to misinterpretations.

Preferred inclination angles α with respect to the planes of the faces are angles of at least 3° or more.

It is advantageous for the edge 33 of semiconductor substrate 3 to be disposed free in space, or to protrude from the support surface of means 11, as shown in FIG. 16, so that light beam 56 can be input without being disturbed.

In order to avoid scattering effects, it has proved to be even more favorable for the light beam to be directed at the substrate from the side facing away from detector 7, as shown in FIG. 16. In other words, the direction of incidence of the light is angled away from the face viewed by detector 30. In this way, light is not incident at the face which faces optical detector 7, so that scattering at superficial structures of this face is avoided, even in the region of impingement of the light beam at the edge of the semiconductor substrate.

It has been found, especially when using lasers, that due to the scattering of the intense infrared light at cracks it is possible to detect even cracks that are covered by overlying opaque structures, such as soldered series connectors, also known as busbars, or by contact fingers.

In solar cells, the light scattered at the crack is reflected at the back contact, or generally at the face facing away from the detector, towards the detector, and so it may exit from the solar cell at an edge of the covering.

Figure 17:
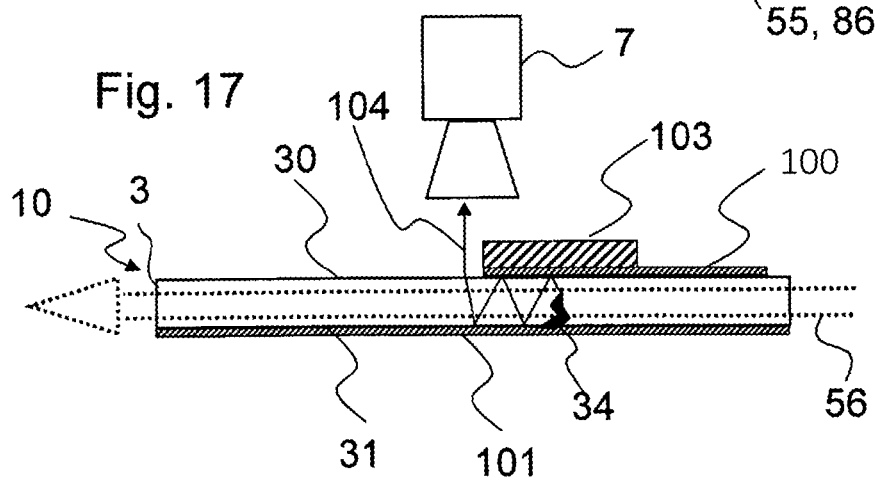
FIG. 17 illustrates another exemplary embodiment of introducing the light.

This will be explained with reference to the example of FIG. 17:

A solar cell 10 comprising a semiconductor substrate 3 has a front contact 100 and a back contact 101. Series connectors 103 are soldered to the front face and also to the back face. For example, series connectors 103 have a width of 2 mm and a thickness of 200 μm. If a crack 34 is located below a series connector 103 which faces the detector so that it cannot be detected directly by detector 7, this crack 34 can nevertheless be detected since a part of the intense laser light is back-scattered at the surface of the semiconductor substrate, the scattered light 104 possibly being reflected several times between the contacts, as shown in FIG. 17.

It is also due to the typically existing microscopic roughness of the semiconductor surfaces that the light may exit from the surface towards IR camera 7, thereby revealing the crack.

Therefore, according to this embodiment of the invention a crack beneath a series connector, or more generally beneath an opaque structure, provided at the face of the semiconductor substrate facing detector 7 is detected by the fact that the edge of the opaque structure gleams when a crack existing below the opaque structure causes light scattering.

It will be obvious for a skilled person that the invention is not limited to the embodiments described above but can be varied in many ways within the scope of the appended claims. In particular, features of individual exemplary embodiments may be combined.

LIST OF REFERENCE NUMERALS

1 apparatus for detecting cracks in planar semiconductor substrates
2 advance direction 3 semiconductor substrate
5 light source
6 bright-field light source
7 optical detector
9 linear area captured by 7
10 solar cell
11 means for supporting 3
13 advance means
15 computing device
30, 31 face of 3
33 edge of 3
34, 340, 341 crack
35 bright area of 3 at the edge of the semiconductor substrate,
36 partial beam of the laser beam
51, 52 infrared laser
53 optical fiber
54 fiber output
55 beam-forming means
56, 57 rays of 51, 52
58, 59 beam widening means
60 light beam from 6
70, 71 line-shaped areas on sensor
72, 73 partial images
76 trigger means
78, 79 masked areas in 72, 73
80 complete image composed of 72, 73
81, 82, 83, 84 trigger pulses
86 collimator
87 beam diameter
100 front side contact of 10
101 back side contact of 10
103 series connector of 10
104 light scattered at 34
342 non-contacted solar cell area
500, 502 lines of light emitting diodes
503 light emitting diode
701 line scan camera

The invention claimed is:

1. A method for detecting cracks in planar, polycrystalline semiconductor substrates that have two opposite faces and a circumferential edge surface, comprising:
    directing electromagnetic radiation into the edge surface of the polycrystalline semiconductor substrate, the electromagnetic radiation having a wavelength that is at least partially transmitted by the polycrystalline semiconductor substrate so that the electromagnetic radiation is directed from the edge surface for at least half a distance to a point opposite the edge surface by reflection at the two opposite faces;
    detecting electromagnetic radiation of at least a portion of one of the two opposite faces with an imaging optical detector that is sensitive to the electromagnetic radiation at the wavelength, wherein the electromagnetic radiation is scattered by the cracks and exits from one of the two opposite faces at sites of the cracks;
    generating an image of scattering intensity from the electromagnetic radiation detected by the imaging optical detector; and
    placing an opaque structure between the face of the polycrystalline semiconductor substrate and the imaging optical detector and recognizing a gleaming periphery of the opaque structure as a crack.

2. The method according to claim 1, further comprising moving the polycrystalline semiconductor substrate and the light source relative to each other in an advance direction along the two opposite faces and transversely to a direction of incidence of the electromagnetic radiation while directing the electromagnetic radiation into the edge surface by the laser such that a point of incidence of the light beam is moved along the edge surface of the polycrystalline semiconductor substrate,
    wherein the image of scattering intensity is generated from the electromagnetic radiation detected by the imaging optical detector during the relative movement.

3. The method according to claim 1, wherein the electromagnetic radiation comprises infrared light having a wavelength of at least 1.2 micrometers.

4. The method according to claim 1, further comprising detecting the cracks by evaluating a local brightness distribution of the image of scattering intensity.

5. The method according to claim 1, wherein the step of directing electromagnetic radiation into the edge surface of the polycrystalline semiconductor substrate comprises directing light of a laser beam into each edge surface.

6. The method according to claim 5, further comprising:
    detecting electromagnetic radiation of a first portion of one of the two opposite faces with the imaging optical detector and generating a first partial image therefrom;
    detecting electromagnetic radiation of a second portion of the one of the two opposite faces with the imaging optical detector and generating a second partial image therefrom; and
    composing a complete image from the two partial images.

7. The method according to claim 5, wherein at least one of the laser beams irradiates the polycrystalline semiconductor substrate at an oblique angle to an advance direction.

8. The method according to claim 1, further comprising performing at least one additional imaging selected from the group consisting of electro-luminescent imaging, photo-luminescent imaging, bright-field imaging, and dark-field imaging.

9. The method according to claim 1, wherein the step of placing the opaque structure between the face of the polycrystalline semiconductor substrate and the imaging optical detector comprises overlying the opaque structure on the face of the polycrystalline semiconductor.

10. The method according to claim 1, wherein the opaque structure comprises a busbar or a contact finger.

11. A method for detecting cracks in planar, polycrystalline semiconductor substrates that have two opposite faces and a circumferential edge surface, comprising:
    directing electromagnetic radiation into the edge surface of the polycrystalline semiconductor substrate, the electromagnetic radiation having a wavelength that is at least partially transmitted by the polycrystalline semiconductor substrate so that the electromagnetic radiation is directed from the edge surface for at least half a distance to a point opposite the edge surface by reflection at the two opposite faces, wherein the step of directing electromagnetic radiation into the edge surface of the polycrystalline semiconductor substrate comprises irradiating the polycrystalline semiconductor substrate with a light beam from a laser as a light source of the electromagnetic radiation, the light beam having a dimension that is larger than a thickness of the polycrystalline semiconductor substrate;
    detecting electromagnetic radiation of at least a portion of one of the two opposite faces with an imaging optical detector that is sensitive to the electromagnetic radiation at the wavelength, wherein the electromagnetic radiation is scattered by the cracks and exits from one of the two opposite faces at sites of the cracks;

generating an image of scattering intensity from the electromagnetic radiation detected by the imaging optical detector; and placing an opaque structure between the face of the polycrystalline semiconductor substrate and the imaging optical detector and recognizing a gleaming periphery of the opaque structure as a crack.

12. An apparatus for detecting cracks in planar, polycrystalline semiconductor substrates that have two opposite faces and a circumferential edge surface, comprising:

a support for the polycrystalline semiconductor substrate;

a radiation source arranged in relationship to the support so that electromagnetic radiation from the radiation source is directed into the edge surface of the polycrystalline semiconductor substrate on the support, the electromagnetic radiation having a wavelength that is at least partially transmitted by the polycrystalline semiconductor substrate on the support;

an imaging optical detector sensitive to the electromagnetic radiation, the imaging optical detector being arranged in relationship to the support so that the imaging optical detector detects electromagnetic radiation that exits from one of the two opposite faces of the polycrystalline semiconductor substrate on the support;

an opaque structure between the face of the polycrystalline semiconductor substrate and the imaging optical detector; and a computing device adapted to generate an image of scattering intensity of at least a portion of the face that is viewed by the imaging optical detector, the computing device being configured to recognize a gleaming periphery of the opaque structure as a crack.

13. The apparatus according to claim 12, wherein the radiation source comprises a laser, the apparatus further comprising:

an advancing device configured to effect movement of the support and the laser relative to each other in a direction along the faces and transversely to the direction of incidence of the light, wherein the computing device is adapted to generate the image of scattering intensity during the relative movement.

14. The apparatus according to claim 13, wherein the laser is fixedly arranged in relation to the imaging optical detector and wherein the advancing device is adapted to move the support relative to the laser and the imaging optical detector.

15. The apparatus according to claim 12, wherein the imaging optical detector comprises one or more area array or linear array sensors.

16. The apparatus according to claim 12, wherein the radiation source generates two beams of electromagnetic radiation in opposite directions.

17. The apparatus according to claim 16, further comprising a trigger configured to intermittently clock the two beams, wherein the imaging optical detector is synchronized with the trigger so that the imaging optical detector intermittently generates detector signals of the scattered light from the two beams.

18. The apparatus according to claim 16, further comprising a trigger configured to intermittently clock the two beams separately from one another, wherein the imaging optical detector is synchronized with the trigger so that the imaging optical detector intermittently generates detector separate signals of the scattered light from each of the two beams.

19. The apparatus according to claim 12, wherein the radiation source generates a beam which illuminates at least one third of the width of the polycrystalline semiconductor substrate on the support.

20. The apparatus according to claim 12, wherein the radiation source is arranged to impinge light at an angle to the faces of the polycrystalline semiconductor substrate on the support.

* * * * *